United States Patent [19]

Newallis et al.

[11] Patent Number: 5,189,195

[45] Date of Patent: Feb. 23, 1993

[54] PROCESS FOR PRODUCING STABLE, LOW ODOR S,S,S-TRIBUTYLPHOSPHOROTRITHIOATE

[75] Inventors: Peter E. Newallis; Vidyanatha A. Prasad, both of Lea Wood; Edward R. Levy, Prairie Village, all of Kans.

[73] Assignee: Miles Inc., Pittsburgh, Pa.

[21] Appl. No.: 738,069

[22] Filed: Jul. 30, 1991

[51] Int. Cl.⁵ .................... C07F 9/02; C07F 9/165
[52] U.S. Cl. ........................ 558/208; 558/71
[58] Field of Search ................... 558/71, 208

[56] References Cited

U.S. PATENT DOCUMENTS

| | | | |
|---|---|---|---|
| 2,206,284 | 7/1940 | Jaynb | 558/208 X |
| 2,828,244 | 3/1958 | Fonner et al. | 558/71 X |
| 2,897,225 | 7/1959 | Tierney et al. | 558/71 |
| 2,943,107 | 6/1960 | Rattenbury et al. | 558/208 |
| 3,259,540 | 7/1966 | Pianka et al. | 558/71 X |
| 3,275,717 | 9/1966 | Butler | 558/71 |
| 3,668,282 | 6/1972 | Below | 558/71 |
| 3,971,836 | 7/1976 | Strow et al. | 558/71 |
| 4,039,636 | 8/1977 | Claus et al. | 558/208 X |
| 4,496,495 | 1/1985 | Caspari et al. | 558/71 |
| 4,650,894 | 3/1987 | Fisch et al. | 558/71 |

*Primary Examiner*—Floyd D. Higel
*Attorney, Agent, or Firm*—Joseph C. Gil; Lyndanne M. Whalen

[57] ABSTRACT

Stable S,S,S-tributylphosphorotrithioate having reduced levels of the odorous by-product dibutyl disulfide is produced by adding a caustic solution having a concentration of less than 10% to crude S,S,S-tributylphosphorotrithioate until the pH remains constant. In a preferred embodiment, a solution of sodium hydroxide having a concentration of less than 10% is used in an amount such that at least 0.1 mole of sodium hydroxide is present for each mole of crude S,S,S-tributylphosphortrithioate.

8 Claims, No Drawings

PROCESS FOR PRODUCING STABLE, LOW ODOR S,S,S-TRIBUTYLPHOSPHOROTRITHIOATE

BACKGROUND OF THE INVENTION

The present invention relates to a process for producing storage-stable, low odor S,S,S-tributylphosphorotrithioate.

S,S,S-tributylphosphorotrithioate is a known cotton defoliant which is produced by reacting phosphorus trichloride with butyl mercaptan and then oxidizing this reaction product. One of the by-products formed when unreacted butyl mercaptan is oxidized is the highly odorous dibutyl disulfide. Dibutyl disulfide is also a by-product formed upon the decomposition of trace amounts of S,S,S-tributylphosphorotrithioite during the oxidation of that material to form the corresponding phosphorotrithioate.

Several approaches have been taken to reduce the levels of dibutyl disulfide formed during the production process and to reduce the residual amounts of dibutyl disulfide present in the product S,S,S-tributylphosphorotrithioate in an effort to reduce the odor problems associated with that material.

In one approach, S,S,S-tributylphosphorotrithioite (the intermediate from which S,S,S-tributylphosphorotrithioate is produced) is produced by reducing the amount of butyl mercaptan used. See, for example, U.S. Pat. No. 2,943,107. In another approach, the phosphorus trichloride and a slight excess of butyl mercaptan are each added simultaneously to a reaction vessel maintained at reaction temperature. See U.S. Ser. No. 07/339,043, filed Apr. 14, 1989.

In each of these processes, however, there is still some unreacted butyl mercaptan present which oxidizes to form the unwanted dibutyl disulfide. This residual disulfide imparts an undesirable odor to the product S,S,S-tributylphosphorotrithioate.

This odor problem is compounded when crude S,S,S-tributylphosphorotrithioate is treated with a caustic material to improve the stability of the final S,S,S-tributylphosphorotrithioate. Unwanted dibutyl disulfide is formed during hydrolysis of crude S,S,S-tributylphosphorotrithioate. If the conditions under which the hydrolysis is carried out are not carefully controlled additional dibutyl disulfide is formed due to the decomposition of the S,S,S-tributylphosphorotrithioate.

SUMMARY OF THE INVENTION

It is an object of the present invention to provide a process for the production of a stable, low odor S,S,S-tributylphosphorotrithioate.

It is also an object of the present invention to provide a process for reducing the amount of dibutyl disulfide present in crude S,S,S-tributylphosphorotrithioate.

These and other objects which will be apparent to those skilled in the art are accomplished by adding a caustic solution having a concentration of less than 10% to crude S,S,S-tributylphosphorotrithioate until the pH is relatively constant.

DETAILED DESCRIPTION OF THE INVENTION

The present invention relates to a process for producing stable, low odor S,S,S-tributylphosphorotrithioate. In this process, a caustic solution having a concentration of less than 10% is added to crude S,S,S-tributylphosphorotrithioate in order to selectively destroy impurities that would adversely affect the stability of the final product.

The caustic solution employed is generally a solution of a strong alkali metal hydroxide, preferably sodium hydroxide. This caustic solution must have a concentration of less than 10%, preferably from about 2.5% to about 5%, and most preferably about 5%. The caustic solution is added until the pH of the product-containing reaction mixture is constant. (The pH is generally about 11.)

Where sodium hydroxide is the caustic solution, it is preferred that the sodium hydroxide (regardless of the concentration of the solution) be added in an amount such that at least about 0.1 moles of sodium hydroxide will be present for each mole crude S,S,S-tributylphosphorotrithioate being treated. The sodium hydroxide could be used in lesser amounts but such lesser amounts compromise the stability characteristics of the final phosphorotrithioate product. It is also preferred that the sodium hydroxide not be used in quantities such that substantially more than 0.1 moles of sodium hydroxide is present for each mole of crude S,S,S-tributylphosphorotrithioate present. No additional improvement with respect to stability of the final product was obtained at these higher levels and the final product contained increased quantities of the unwanted dibutyl disulfide.

The crude S,S,S-tributylphosphorotrithioate may be prepared by any of the techniques known to those skilled in the art. In the known techniques, phosphorus trichloride is reacted with butyl mercaptan. The butyl mercaptan is generally used in excess. This reaction is generally carried out at a temperature of from about 90° C. to about 115° C. The S,S,S-tributylphosphorithioite thus formed is then oxidized to form crude S,S,S-tributylphosphorotrithioate. Suitable oxidizing agents include: air, hydrogen peroxide, perborates and persulfates.

The crude S,S,S-tributylphosphorotrithioate is then treated with a caustic solution having a concentration of less than 10% to maintain the level of dibutyl disulfide present therein to less than 0.40%, preferably to less than 0.30%.

The final product is recovered from the caustic/crude phosphorotrithioate mixture by standard techniques such as phase separations. It has been found that use of sodium hydroxide solutions having concentrations of from about 2.5% to about 5% are particularly advantageous not only because substantially reduced levels of dibutyl disulfide are present in the final product but also because they make it easier to recover the product S,S,S-tributylphosphorotrithioate by phase separation techniques.

Having thus described our invention, the following examples are given as being illustrative thereof. All parts and percentages are parts and percentages by weight, unless otherwise indicated.

EXAMPLES

The crude S,S,S-tributylphosphorotrithioate used in each of these examples was prepared by adding one mole of phosphorus trichloride per 3.36 moles of butyl mercaptan to a reactor maintained at a temperature of about 115° C. in the presence of nitrogen for a period of 8 hours to form S,S,S-tributylphosphorotrithioite. After removal of as much of the excess butyl mercaptan as possible, the S,S,S-tributylphosphorotrithioite was oxidized by adding peroxide dropwise over a period of one hour to the reactor which was maintained at a temperature of from 30°–32° C. This mixture was then heated to a temperature of about 41° C. and maintained at that temperature for one hour. The mixture was then neutralized by adding sodium bisulfite while cooling. The crude S,S,S-tributylphosphorotrithioate was then separated from the aqueous phase.

The storage stability of all samples generated in the following Examples was monitored by measuring the levels of n-butylmercaptan produced by those samples when maintained at a temperature of 60° C. in a constant temperature oven for a given period of time. The length of time for which the level of n-butylmercaptan remained constant is reported as the period for which the sample was storage stable.

EXAMPLE 1

A 5% solution of sodium hydroxide was added to the crude S,S,S-tributylphosphorotrithioate in an amount such that 0.1 mole of sodium hydroxide for each mole of crude S,S,S,-tributylphosphorotrithioate present. Upon completion of the addition of the sodium hydroxide, the pH of the mixture remained constant at 11. This mixture was then heated at a temperature of 60° C. for one hour and cooled to ambient temperature. Concentrated hydrochloric acid was then added until the pH remained constant at 4.5. The mixture was allowed to stand until the S,S,S,-tributylphosphorotrithioate separated. The S,S,S-tributylphosphorotrithioate was then recovered and analyzed by gas chromatography. The results of this anaylsis were as follows:

| | | |
|---|---|---|
| Dibutyl disulfide | 0.363% (wet) | 0.373% (water-free basis) |
| S,S,S-tributyl-phosphorotrithioate | 96.854% (wet) | 99.437% (water-free basis) |
| Water | 2.598% (wet) | |
| BuSH | 0.185% (wet) | 0.190% (water-free basis) |

The S,S,S-tributylphosphorotrithioate thus obtained was storage stable for the entire test period of 21 days.

EXAMPLE 2 (COMPARATIVE)

The procedure of Example 1 was repeated with the exception that a 10% sodium hydroxide solution (instead of the 5% solution) was used. The analysis of the product was as follows:

| | | |
|---|---|---|
| Dibutyl disulfide | 0.580% (wet) | 0.594% (water-free basis) |
| S,S,S-tributyl-phosphorotrithioate | 96.727% (wet) | 99.118% (water-free basis) |
| Water | 2.412% (wet) | |
| BuSH | 0.282% (wet) | 0.289% (water-free basis) |

The S,S,S-tributylphosphorotrithioate thus obtained was storage stable for the entire test period of 21 days.

EXAMPLE 3

The relationship between the number of moles of sodium hydroxide per mole of crude S,S,S-tributylphosphorotrithioate, concentration of sodium hydroxide solution employed and amount of dibutyl disulfide present in the final product were studied by adding sodium hydroxide solutions of varying concentrations in varying amounts to crude S,S,S,-tributylphosphorotrithioate. The molar amounts of sodium hydroxide per mole of crude phosphorotrithioate (designated "Moles" in Table I), concentrations of the sodium hydroxide solutions (designated "Concentration" in Table I) and the relative amount of dibutyl disulfide present in the final product after work up and drying (designated % Dibutyldisulfide in Table I) are reported in Table I.

TABLE I

| Moles | Concentration | % Dibutyldisulfide |
|---|---|---|
| 0.15 | 10% | 0.69% |
| 0.10 | 10% | 0.56% |
| 0.05 | 10% | 0.51% |
| 0.15 | 5% | 0.36% |
| 0.10 | 5% | 0.28% |
| 0.05 | 5% | 0.24% |
| 0.15 | 2.5% | 0.33% |
| 0.10 | 2.5% | 0.26% |
| 0.05 | 2.5% | 0.21% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing stable S,S,S-tributylphosphorotrithioate having reduced levels of dibutyl disulfide comprising adding a caustic solution to crude S,S,S-tributylphosphorotrithioate which caustic solution has a concentration of less than 10% in an amount sufficient to obtain a constant pH.

2. The process of claim 1 in which the caustic solution is a solution of sodium hydroxide.

3. The process of claim 2 in which the sodium hydroxide is added in an amount such that about 0.1 mole of sodium hydroxide is present for each mole of crude S,S,S-tributylphosphorotrithioate.

4. The process of claim 2 in which the solution has a concentration of from about 2.5% to about 5%.

5. The process of claim 4 in which the sodium hydroxide is added in an amount such that about 0.1 mole of sodium hydroxide is present for each mole of crude S,S,S-tributylphosphorotrithioate.

6. The process of claim 1 in which the caustic solution is a 5% sodium hydroxide solution.

7. The process of claim 6 in which the sodium hydroxide is added in an amount such that 0.1 mole of sodium hydroxide is present for each mole of crude S,S,S-tributylphosphorotrithioate.

8. The process of claim 6 in which the caustic solution is added until a constant pH of approximately 11 is obtained.

* * * * *